United States Patent
Kaneko et al.

(10) Patent No.: US 11,370,760 B2
(45) Date of Patent: Jun. 28, 2022

(54) DITHIOESTER COMPOUND

(71) Applicant: Sumitomo Rubber Industries, Ltd., Kobe (JP)

(72) Inventors: Takumi Kaneko, Kobe (JP); Takahiro Shigemitsu, Kobe (JP); Kazuyoshi Shiga, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 0 days.

(21) Appl. No.: 17/125,007

(22) Filed: Dec. 17, 2020

(65) Prior Publication Data
US 2021/0188780 A1    Jun. 24, 2021

(30) Foreign Application Priority Data
Dec. 18, 2019   (JP) .............................. JP2019-228268

(51) Int. Cl.
*C07D 231/12* (2006.01)

(52) U.S. Cl.
CPC .................................. *C07D 231/12* (2013.01)

(58) Field of Classification Search
CPC .................................................... C07D 231/12
See application file for complete search history.

(56) References Cited

PUBLICATIONS

Kulka, Marshall. 'Hydrolysis and hydrazinolysis of esters of N,N-dimethyldithiocarbamic acid—a method for the preparation of mercaptans', 1956, vol. 34, pp. 1093-1100. (abstract) [online] [retrieved on Sep. 21, 2021]. Retrieved from STNext, Accession No. 1957:17045 ZCAPLUS.*

Gardiner et al., "Dithiocarbamate RAFT agents with broad applicability—the 3,5-dimethyl-1H-pyrazole-1-carbodithioates", Polymer Chemistry, England, 2016, vol. 7, pp. 481-492.

Kato et al., "Thioacylsulfenyl Bromides: Electrophilic Dithiocarboxylating Reagents", Tetrahedron Letters, England, 1986, vol. 27, No. 38, pp. 4595-4598.

Tsai et al., "PIFA-Mediated Synthesis of Acylsulfenic Acid Alkyl Esters and Benzoyl Alkyl Disulfides from Thioacids", Synthesis, US, 2016, vol. 48, pp. 4459-4464.

\* cited by examiner

*Primary Examiner* — Shawquia Jackson
(74) *Attorney, Agent, or Firm* — Birch, Stewart, Kolasch & Birch, LLP

(57) ABSTRACT

An object of the present invention is to provide a dithioester compound generating an aralkyloxy radical having high ability of abstracting hydrogen. The present invention provides a dithioester compound represented by a formula (1).

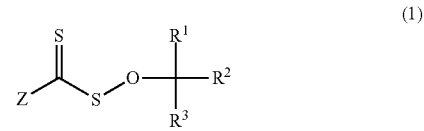

(1)

In the formula (1), $R^1$ and $R^2$ each independently represent an alkyl group having 1 or more carbon atoms, an alkenyl group having two or more carbon atoms, an alkynyl group having two or more carbon atoms, an aryl group having 6 or more carbon atoms and optionally having a substituent group, an aralkyl group having 6 or more carbon atoms, a hydrogen atom, or a halogen atom; $R^3$ represents an aryl group having 6 or more carbon atoms and optionally having a substituent group, or an aralkyl group having 6 or more carbon atoms and optionally having a substituent group.

20 Claims, 4 Drawing Sheets

DITHIOESTER COMPOUND

FIELD OF THE INVENTION

The present invention relates to a novel dithioester compound.

DESCRIPTION OF THE RELATED ART

Among dithioester compounds, there is a compound utilized to control radical polymerization as a reversible addition fragmentation chain transfer agent (RAFT agent). Such RAFT agent is a compound having a thiocarbonylthio group (S=C—S) with an organic group R and an organic group Z as a substituent group, and has a structure of Z—C(=S)—S—R. R cleaves to generate a radical (R.), and this radical has an ability of reacting with a monomer to re-initiate polymerization. Z affects the stability of the intermediate radical, and controls the reactivity of the thiocarbonyl group (C=S) of the RAFT agent to free radical addition.

A general RAFT agent has a structure for polymerization in a solution. In addition, in a controlled radical polymerization (RAFT polymerization) utilizing a RAFT agent, from the viewpoint of controlling the polymerization, a radical generated from the RAFT agent is required to cause an addition reaction to a monomer without a side reaction. A radical generated from an azo type radical initiator is believed to relatively hardly cause a side reaction. Thus, the RAFT agent molecule has been designed to generate a radical which has the structure similar to the radical generated from the azo type radical initiator.

In addition, regarding the method for synthesizing the dithioester compound, various methods have been proposed. For example, Polymer Chemistry, p. 481 to 492, Volume $7^{th}$, 2016 (UK) discloses a method of carrying out a reaction between a dithioester potassium salt and an alkyl chloride to obtain a RAFT agent. Tetrahedron Letters, p. 4595 to 4598, No. 38, Volume $27^{th}$, 1986 (UK) discloses a method of synthesizing a tin complex, carrying out a reaction between the tin complex and N-bromosuccinimide to brominate the tin complex, followed by a reaction between the brominated product and an alcohol to synthesize a dithioester peroxide. Synthesis, p. 4459 to 4464, Volume $48^{th}$, 2016 (USA) discloses a method of synthesizing a sulfenic acid ester using a hypervalent iodine reagent.

SUMMARY OF THE INVENTION

The general RAFT agent molecule has been designed to generate a radical with a relatively less side reaction. However, such a radical with a relatively less side reaction has low ability of abstracting hydrogen. Thus, for example, in case of using the RAFT agent as an additive for synthesizing a polymer material having a crosslinked structure, the usage of the RAFT agent is considered to be a factor of lowering the forming efficiency of the crosslinked structure. The present invention has been made in view of the above problems. An object of the present invention is to provide a novel dithioester compound generating an aralkyloxy radical having high ability of abstracting hydrogen.

The present invention that has solved the above problem provides a dithioester compound represented by a formula (1).

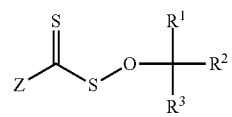
(1)

[In the formula (1), $R^1$ and $R^2$ each independently represent an alkyl group having 1 or more carbon atoms, an alkenyl group having two or more carbon atoms, an alkynyl group having two or more carbon atoms, an aryl group having 6 or more carbon atoms with an optional substituent group, an aralkyl group having 6 or more carbon atoms with an optional substituent group, a hydrogen atom, or a halogen atom.

$R^3$ represents an aryl group having 6 or more carbon atoms with an optional substituent group, or an aralkyl group having 6 or more carbon atoms with an optional substituent group.

Z represents an alkyl group, an alkenyl group, an alkynyl group, an aryl group, an aralkyl group, a heterocyclyl group, an alkoxy group, an aryloxy group, an aralkyloxy group, a heterocyclyloxy group, an alkanoyl group, an aroyl group, a heterocyclylcarbonyl group, an alkoxycarbonyl group, an aryloxycarbonyl group, a heterocyclyloxycarbonyl group, an alkanoyloxy group, an aroyloxy group, a heterocyclylcarbonyloxy group, a carbamoyl group, a carboxy group, an alkylthio group, an arylthio group, an amino group, a cyano group, a dialkylphosphonate group, a diarylphosphonate group, a dialkylphosphinate group, a diarylphosphinate group, an organic group having a part of hydrogen atoms of these organic groups being substituted, a hydrogen atom, or a halogen atom.]

The dithioester compound according to the present invention generates an aralkyloxy radical ($R^1R^2R^3CO.$) having high ability of abstracting hydrogen. Thus, the dithioester compound according to the present invention is suitably used as an additive (RAFT agent) when synthesizing a polymer material having a crosslinked structure.

According to the present invention, a dithioester compound generating an aralkyloxy radical having high ability of abstracting hydrogen is obtained.

DESCRIPTION OF THE PREFERRED EMBODIMENT

[Dithioester Compound]

Figure 1:
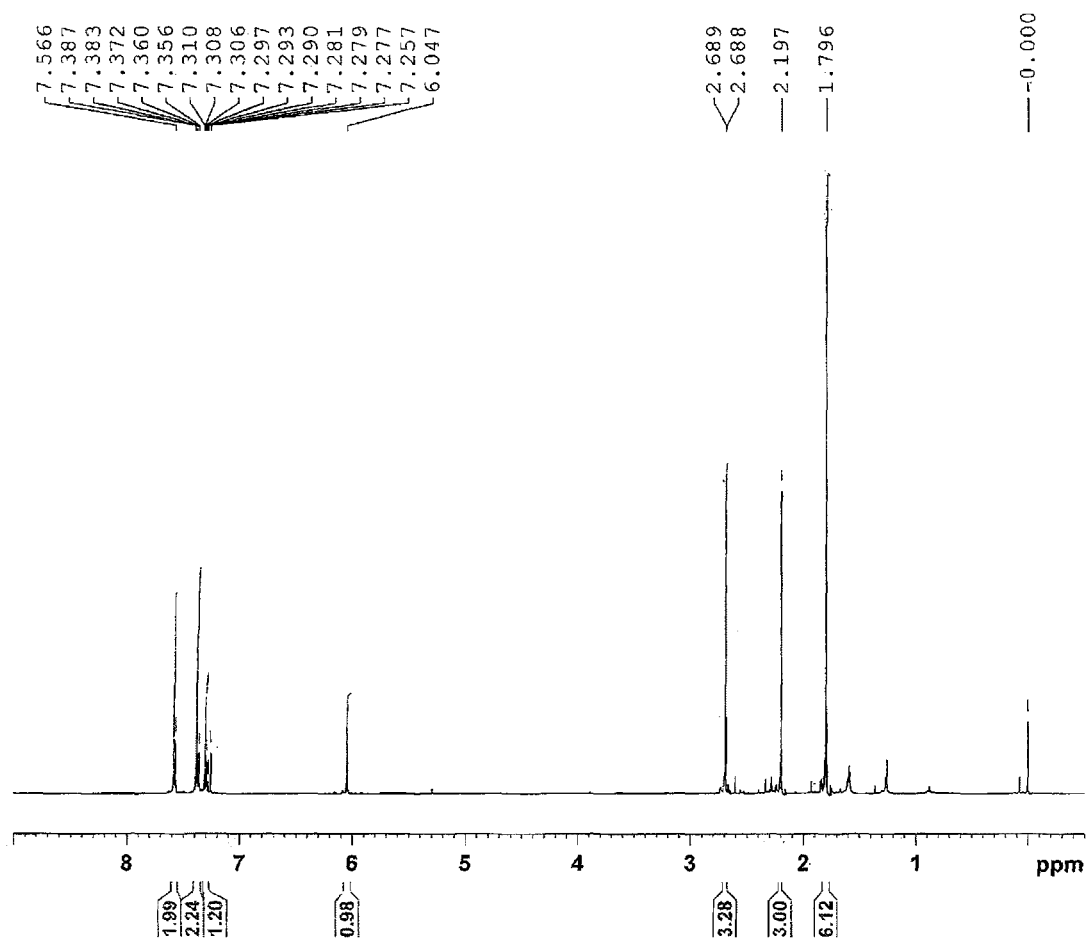
FIG. 1 is $^1$H-NMR spectrum of dithioester compound No. 1.

The present invention provides a dithioester compound represented by a formula (1).

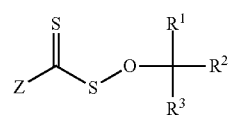
(1)

[In the formula (1), $R^1$ and $R^2$ each independently represent an alkyl group having 1 or more carbon atoms, an alkenyl group having two or more carbon atoms, an alkynyl group having two or more carbon atoms, an aryl group having 6 or more carbon atoms with an optional substituent group, an aralkyl group having 6 or more carbon atoms with an optional substituent group, a hydrogen atom, or a halogen atom.

$R^3$ represents an aryl group having 6 or more carbon atoms with an optional substituent group, or an aralkyl group having 6 or more carbon atoms with an optional substituent group.

Z represents an alkyl group, an alkenyl group, an alkynyl group, an aryl group, an aralkyl group, a heterocyclyl group, an alkoxy group, an aryloxy group, an aralkyloxy group, a heterocyclyloxy group, an alkanoyl group, an aroyl group, a heterocyclylcarbonyl group, an alkoxycarbonyl group, an aryloxycarbonyl group, a heterocyclyloxycarbonyl group, an alkanoyloxy group, an aroyloxy group, a heterocyclylcarbonyloxy group, a carbamoyl group, a carboxy group, an alkylthio group, an arylthio group, an amino group, a cyano group, a dialkylphosphonate group, a diarylphosphonate group, a dialkylphosphinate group, a diarylphosphinate group, an organic group having a part of hydrogen atoms of these organic groups being substituted, a hydrogen atom, or a halogen atom.]

Examples of the alkyl group having 1 or more carbon atoms represented by the above $R^1$ and $R^2$ include a linear alkyl group, a branched alkyl group, and a cyclic alkyl group. The number of carbon atoms of the alkyl group is preferably 15 or less, more preferably 10 or less, and even more preferably 5 or less. Examples of the linear alkyl group include a methyl group, an ethyl group, a n-propyl group, a n-butyl group, and a n-pentyl group. Examples of the branched alkyl group include an isopropyl group, an isobutyl group, and a t-butyl group. Examples of the cyclic alkyl group include a cyclopropyl group, a cyclobutyl group, a cyclopentyl group, and a cyclohexyl group.

Examples of the alkenyl group having two or more carbon atoms represented by the above $R^1$ and $R^2$ include a linear alkenyl group, a branched alkenyl group, and a cyclic alkenyl group. The number of carbon atoms of the alkenyl group is preferably 15 or less, more preferably 10 or less, and even more preferably 5 or less. Examples of the alkenyl group include a vinyl group, a propenyl group, a butenyl group, and a pentenyl group.

Examples of the alkynyl group having two or more carbon atoms represented by the above $R^1$ and $R^2$ include a linear alkynyl group, a branched alkynyl group, and a cyclic alkynyl group. The number of carbon atoms of the alkynyl group is preferably 15 or less, more preferably 10 or less, and even more preferably 5 or less. Examples of the alkynyl group include an ethynyl group, a propynyl group, a butynyl group, and a pentynyl group.

Examples of the halogen atom represented by the above $R^1$ and $R^2$ include fluorine atom, chlorine atom, bromine atom, and iodine atom.

Examples of the aryl group having 6 or more carbon atoms with an optional substituent group represented by the above $R^1$ to $R^3$ include a monocyclic aryl group, and a polycyclic aryl group. The number of carbon atoms of the aryl group is preferably 14 or less, more preferably 10 or less. Examples of the aryl group include a phenyl group, and a naphthyl group. It is noted that a hydrogen atom of the aryl group is optionally substituted with an alkyl group, an alkenyl group, an alkynyl group, an aryl group, an aralkyl group, or a halogen atom.

The number of carbon atoms of the aralkyl group having 6 or more carbon atoms with an optional substituent group represented by the above $R^1$ to $R^3$ is preferably 15 or less, more preferably 11 or less. The aralkyl group is a group having at least one hydrogen atom of an alkyl group being substituted with an aryl group. Examples of the aryl group of the aralkyl group include a monocyclic aryl group, and a polycyclic aryl group. The alkylene group of the aralkyl group is either linear or branched. Examples of the aralkyl group include a benzyl group, a phenylethyl group, a phenylpropyl group, a phenylbutyl group, an α-cumyl group, and a 1-phenylethyl group. It is noted that a hydrogen atom of the aryl group of the aralkyl group is optionally substituted with an alkyl group, an alkenyl group, an alkynyl group, an aryl group, an aralkyl group, or a halogen atom.

In the formula (1), $R^1$ and $R^2$ are preferably the alkyl group having 1 or more carbon atoms, more preferably the alkyl group having 1 to 5 carbon atoms, and most preferably a methyl group, an ethyl group, a propyl group, an isopropyl group, a n-butyl group, a s-butyl group, a t-butyl group, a n-pentyl group, a s-pentyl group, a t-pentyl group, a 3-pentyl group, an isopentyl group, or a neopentyl group.

In the formula (1), $R^3$ is preferably the aryl group having 6 or more carbon atoms with an optional substituent group, more preferably a phenyl group with an optional substituent group.

In the formula (1), $R^3$ is preferably a structure represented by a formula (2).

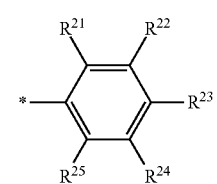

(2)

[in the formula (2), $R^{21}$ to $R^{25}$ each independently represent an alkyl group having 1 or more carbon atoms, an alkenyl group having two or more carbon atoms, an alkynyl group having two or more carbon atoms, an aryl group having 6 or more carbon atoms, an aralkyl group having 6 or more carbon atoms, a hydrogen atom, or a halogen atom.]

Examples of the alkyl group having 1 or more carbon atoms, alkenyl group having two or more carbon atoms, alkynyl group having two or more carbon atoms, aryl group having 6 or more carbon atoms and aralkyl group having 6 or more carbon atoms represented by $R^{21}$ to $R^{25}$ in the formula (2) include those exemplified as $R^1$ to $R^3$ in the formula (1). In the formula (2), $R^{21}$ to $R^{25}$ are preferably an alkyl group having 1 or more carbon atoms or a hydrogen atom, more preferably a hydrogen atom.

Examples of the organic group represented by the above Z include the following groups.

The alkyl group includes a linear alkyl group, a branched alkyl group, and a cyclic alkyl group. The alkyl group preferably has 18 or less carbon atoms. Examples of the alkyl group include a methyl group, an ethyl group, a propyl group, an isopropyl group, a butyl group, a t-butyl group, a dodecyl group, a cyclopentyl group, and a cyclohexyl group.

The alkenyl group includes a linear alkenyl group, a branched alkenyl group, and a cyclic alkenyl group. The alkenyl group preferably has 18 or less carbon atoms. Examples of the alkenyl group include a vinyl group, a propenyl group, a butenyl group, and a pentenyl group.

The alkynyl group includes a linear alkynyl group, a branched alkynyl group, and a cyclic alkynyl group. The alkynyl group preferably has 18 or less carbon atoms. Examples of the alkynyl group include an ethynyl group, a propynyl group, a butynyl group, and a pentynyl group.

The aryl group includes a monocyclic aryl group, and a polycyclic aryl group. The aryl group preferably has 20 or less carbon atoms. Examples of the aryl group include a phenyl group, and a naphthyl group.

The aryl group included in the aralkyl group includes a monocyclic aryl group, and a polycyclic aryl group. The aralkyl group preferably has 20 or less carbon atoms. Examples of the aralkyl group include a benzyl group, a phenylethyl group, a phenylpropyl group, a phenylbutyl group, an α-cumyl group, and a 1-phenylethyl group.

The heterocyclyl group is a group removing one hydrogen atom from any ring-forming atom of a heterocyclic compound. The heterocyclic compound is a cyclic compound having a carbon atom and an atom other than the carbon atom as ring-forming atoms, and is preferably a four-membered ring to a seven-membered ring. The atom constituting the heterocyclic compound other than the carbon atom is preferably one member selected from the group consisting of a nitrogen atom, an oxygen atom and a sulfur atom. Examples of the heterocyclyl group include a pyrrolidyl group, a piperidyl group, a pyrrolyl group, a pyridyl group, a tetrahydrofuryl group, a tetrahydropyranyl group, a furyl group, a tetrahydrothienyl group, a tetrahydrothiopyranyl group, a thienyl group, an imidazolidinyl group, an imidazolilyl group, an imidazolyl group, a pyrazolyl group, an oxazolidinyl group, an oxazolyl group, a thiazolidinyl group, a thiazolyl group, a piperazyl group, a morpholyl group, a pyridazinyl group, a pyrimidinyl group, a pyrazinyl group, a quinolyl group, an isoquinolyl group, and a quinazolinyl group.

The alkoxy group preferably has 18 or less carbon atoms. Examples of the alkoxy group include a methoxy group, an ethoxy group, a propoxy group, and a butoxy group.

The aryloxy group preferably has 20 or less carbon atoms. Examples of the aryloxy group include a phenoxy group.

The aralkyloxy group preferably has 20 or less carbon atoms. Examples of the aralkyloxy group include an α-cumyloxy group.

Examples of the heterocyclyloxy group include a pyrrolyloxy group, a pyridyloxy group, and a pyrimidinyloxy group.

The alkanoyl group preferably has 18 or less carbon atoms. Examples of the alkanoyl group include a formyl group, an acetyl group, a propionyl group, and a butylyl group.

The aroyl group preferably has 20 or less carbon atoms. Examples of the aroyl group include a benzoyl group, and a naphthoyl group.

Examples of the heterocyclylcarbonyl group include a pyrrolylcarbonyl group, a pyridylcarbonyl group, and a pyrimidylcarbonyl group.

The alkoxycarbonyl group preferably has 19 or less carbon atoms. Examples of the alkoxycarbonyl group include a methoxycarbonyl group, an ethoxycarbonyl group, and a propoxycarbonyl group.

The aryloxycarbonyl group preferably has 21 or less carbon atoms. Examples of the aryloxycarbonyl group include a phenoxycarbonyl group.

Examples of the heterocyclyloxycarbonyl group include a pyrrolyloxycarbonyl group, a pyridyloxycarbonyl group, and a pyrimidinyloxycarbonyl group.

The alkanoyloxy group has 18 or less carbon atoms. Examples of the alkanoyloxy group include an acetyloxy group, and a propionyloxy group.

The aroyloxy group preferably has 20 or less carbon atoms. Examples of the aroyloxy group include a benzoyloxy group, and a 1-naphthoyloxy group.

Examples of the heterocyclylcarbonyloxy group include a pyrrolylcarbonyloxy group, a pyridylcarbonyloxy group, and a pyrimidinylcarbonyloxy group.

The alkylthio group has 18 or less carbon atoms. Examples of the alkylthio group include a methylthio group, an ethylthio group, a propylthio group, and a dodecylthio group.

The arylthio group has 20 or less carbon atoms. Examples of the arylthio group include a phenylthio group.

Examples of the substituent group of the organic group having a part of hydrogen atoms of the above organic groups being substituted include an alkyl group, an alkenyl group, an alkynyl group, an aryl group, an aralkyl group, a heterocyclyl group, an alkoxy group, an aryloxy group, an aralkyloxy group, a heterocyclyloxy group, an alkanoyl group, an aroyl group, a heterocyclylcarbonyl group, an alkoxycarbonyl group, an aryloxycarbonyl group, a heterocyclyloxycarbonyl group, an alkanoyloxy group, an aroyloxy group, a heterocyclylcarbonyloxy group, a carbamoyl group, a carboxy group, an alkylthio group, an arylthio group, an amino group, a cyano group, an oxo group, and a halogen atom.

Examples of the organic group having a part of hydrogen atoms of the above organic groups being substituted include a cyanoalkyl group, a halogenated alkyl group, and an alkylamino group, and specific examples thereof include an oxopyrrolidine-1-yl group, a methylphenylamino group, a methylpyridylamino group, a 3,5-dimethylpyrazolyl group, a 4-chloro-3,5-dimethylpyrazolyl group, a cyanomethyl group, a 2-cyanobutane-2-yl group, a 1-cyanoethane-1-yl group, a 2-cyanopropane-2-yl group, a 2-phenylpropane-2-yl group, a 1-cyano-1-phenylethane-1-yl group, and a 2-(ethoxycarbonyl)propane-2-yl group.

Examples of the halogen atom include fluorine atom, chlorine atom, bromine atom, and iodine atom.

In the formula (1), Z is preferably an alkyl group having 1 to 18 carbon atoms, an alkoxy group having 1 to 18 carbon atoms, an aryloxy group having 6 to 20 carbon atoms, or a structure represented by formulae (11) to (16).

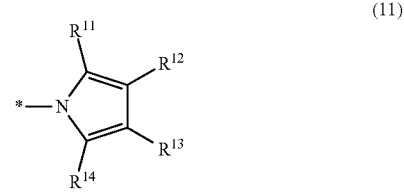

(11)

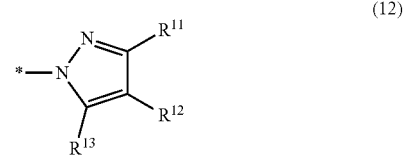

(12)

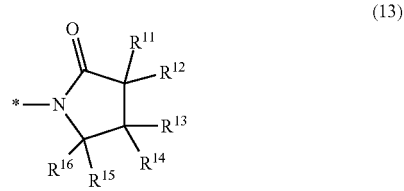

(13)

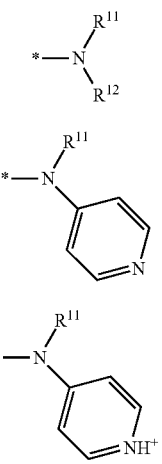

(14)

(15)

(16)

[In the formulae (11) to (16), $R^{11}$ to $R^{16}$ represent an alkyl group having 1 to 18 carbon atoms, an aryl group having 6 to 20 carbon atoms, an aralkyl group having 6 to 20 carbon atoms, a hydrogen atom, or a halogen atom.]

The compound represented by the formula (1) is particularly preferably a compound represented by a formula (3). The intermediate radical is stabilized by the resonance effect or inductive effect by having a pyrazol ring in the Z moiety in the formula (1).

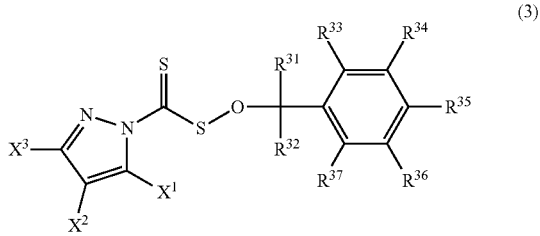

(3)

[In the formula (3), $R^{31}$ to $R^{37}$ each independently represent an alkyl group having 1 or more carbon atoms, an alkenyl group having two or more carbon atoms, an alkynyl group having two or more carbon atoms, an aryl group having 6 or more carbon atoms, an aralkyl group having 6 or more carbon atoms, a hydrogen atom, or a halogen atom;

$X^1$ to $X^3$ each independently represent an alkyl group having 1 or more carbon atoms, an aryl group having 6 or more carbon atoms, an aralkyl group having 6 or more carbon atoms, a hydrogen atom, or a halogen atom.]

Examples of the alkyl group having 1 or more carbon atoms, alkenyl group having two or more carbon atoms, alkynyl group having two or more carbon atoms, aryl group having 6 or more carbon atoms and aralkyl group having 6 or more carbon atoms represented by $R^{31}$ or $R^{32}$ in the formula (3) include those exemplified as $R^1$ or $R^2$ in the formula (1). In the formula (3), $R^{31}$ and $R^{32}$ are preferably an alkyl group having 1 or more carbon atoms, more preferably an alkyl group having 1 to 5 carbon atoms, and most preferably a methyl group, an ethyl group, a propyl group, an isopropyl group, a n-butyl group, a s-butyl group, a t-butyl group, a n-pentyl group, a s-pentyl group, a t-pentyl group, a 3-pentyl group, an isopentyl group, or a neopentyl group.

Examples of the alkyl group having 1 or more carbon atoms, alkenyl group having two or more carbon atoms, alkynyl group having two or more carbon atoms, aryl group having 6 or more carbon atoms and aralkyl group having 6 or more carbon atoms represented by $R^{33}$ to $R^{37}$ in the formula (3) include those exemplified as $R^{21}$ to $R^{25}$ in the formula (2). In the formula (3), $R^{33}$ to $R^{37}$ are preferably an alkyl group having 1 or more carbon atoms or a hydrogen atom, more preferably a hydrogen atom.

Examples of the alkyl group having 1 or more carbon atoms represented by $X^1$ to $X^3$ in the formula (3) include a linear alkyl group, a branched alkyl group, and a cyclic alkyl group. The number of carbon atoms of the alkyl group having 1 or more carbon atoms is preferably 18 or less, more preferably 12 or less. Examples of the alkyl group include a methyl group, an ethyl group, a propyl group, an isopropyl group, a butyl group, a t-butyl group, a dodecyl group, a cyclopentyl group, and a cyclohexyl group.

Examples of the aryl group having 6 or more carbon atoms represented by $X^1$ to $X^3$ in the formula (3) include a monocyclic aryl group, and a polycyclic aryl group. The number of carbon atoms of the aryl group having 6 or more carbon atoms is preferably 20 or less, more preferably 14 or less. Examples of the aryl group include a phenyl group, and a naphthyl group.

Examples of the aryl group of the aralkyl group having 6 or more carbon atoms represented by $X^1$ to $X^3$ in the formula (3) include a monocyclic aryl group, and a polycyclic aryl group. The number of carbon atoms of the aralkyl group having 6 or more carbon atoms is preferably 20 or less, more preferably 15 or less. Examples of the aralkyl group include a benzyl group, a phenylethyl group, a phenylpropyl group, a phenylbutyl group, an α-cumyl group, and a 1-phenylethyl group.

$X^1$ to $X^3$ in the formula (3) are preferably an alkyl group having 1 or more carbon atoms or a hydrogen atom.

Other Embodiment

It is considered that, similar to the dithioester compound according to the present invention, a dithioester compound represented by a formula (21) or a formula (22) generates a radical having high ability of abstracting hydrogen.

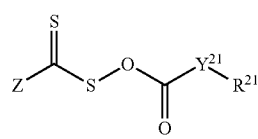

(21)

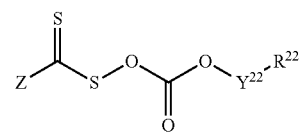

(22)

[In the formulae (21) and (22), $R^{21}$ and $R^{22}$ represent an aryl group with an optional substituent group; $Y^{21}$ and $Y^{22}$ represent an alkylene group having 10 or less carbon atoms, an alkenylene group having 10 or less carbon atoms, —$R^{23}$—C(=O)—$R^{24}$—, or a single bond; and $R^{23}$ and $R^{24}$ represent an alkylene group having 10 or less carbon atoms, or an alkenylene group having 10 or less carbon atoms. The substituent group of the aryl group is an alkyl group having 1 to 12 carbon atoms, an alkenyl group having 2 to 13 carbon atoms, an alkynyl group having 2 to 13 carbon atoms, a carboxy group, or a halogen atom.

Z represents an alkyl group, an alkenyl group, an alkynyl group, an aryl group, an aralkyl group, a heterocyclyl group, an alkoxy group, an aryloxy group, an aralkyloxy group, a heterocyclyloxy group, an alkanoyl group, an aroyl group, a heterocyclylcarbonyl group, an alkoxycarbonyl group, an aryloxycarbonyl group, a heterocyclyloxycarbonyl group, an alkanoyloxy group, an aroyloxy group, a heterocyclylcarbonyloxy group, a carbamoyl group, a carboxy group, an alkylthio group, an arylthio group, an amino group, a cyano group, a dialkylphosphonate group, a diarylphosphonate group, a dialkylphosphinate group, a diarylphosphinate group, an organic group having a part of hydrogen atoms of these organic groups being substituted, a hydrogen atom, or a halogen atom.

It is noted that the alkyl group, alkenyl group, alkynyl group, alkylene group and alkenylene group include a linear group and a branched group.]

The dithioester compound represented by the formula (21) or the formula (22) is preferably a compound represented by a formula (23) or a formula (24).

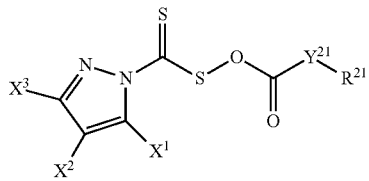
(23)

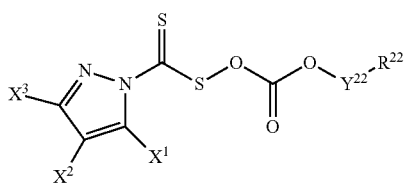
(24)

[In the formulae (23) and (24), $R^{21}$ and $R^{22}$ represent an aryl group with an optional substituent group; $Y^{21}$ and $Y^{22}$ represent an alkylene group having 10 or less carbon atoms, an alkenylene group having 10 or less carbon atoms, —$R^{23}$—C(=O)—$R^{24}$—, or a single bond; and $R^{23}$ and $R^{24}$ represent an alkylene group having 10 or less carbon atoms, or an alkenylene group having 10 or less carbon atoms. The substituent group of the aryl group is an alkyl group having 1 to 12 carbon atoms, an alkenyl group having 2 to 13 carbon atoms, an alkynyl group having 2 to 13 carbon atoms, a carboxy group, or a halogen atom.

$X^1$ to $X^3$ each independently represent an alkyl group having 1 or more carbon atoms, an aryl group having 6 or more carbon atoms, an aralkyl group having 6 or more carbon atoms, a hydrogen atom, or a halogen atom.

It is noted that the alkyl group, alkenyl group, alkynyl group, alkylene group and alkenylene group include a linear group, a branched group, and a cyclic group.]

Examples of the dithioester compound represented by the formula (23) include the following compounds.

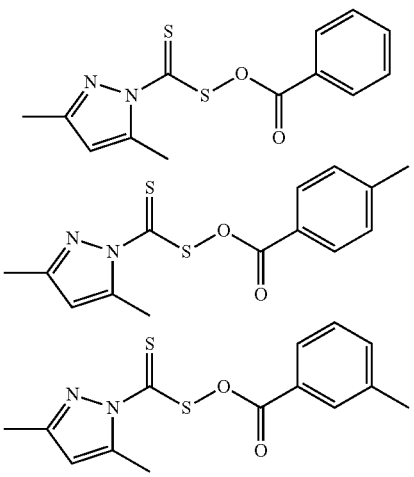

[Production Method of Dithioester Compound]

The method for producing the dithioester compound according to the present invention comprises carrying out a reaction between a dithiocarboxylic acid metal salt represented by a formula (4) (hereinafter, sometimes simply referred to as "dithiocarboxylic acid metal salt".) and an alcohol represented by a formula (5) (hereinafter, sometimes simply referred to as "alcohol".) in the presence of [bis(trifluoroacetoxy)iodo]benzene.

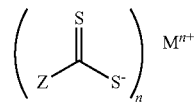
(4)

[In the formula (4), Z represents an alkyl group, an alkenyl group, an alkynyl group, an aryl group, an aralkyl group, a heterocyclyl group, an alkoxy group, an aryloxy group, an aralkyloxy group, a heterocyclyloxy group, an alkanoyl group, an aroyl group, a heterocyclylcarbonyl group, an alkoxycarbonyl group, an aryloxycarbonyl group, a heterocyclyloxycarbonyl group, an alkanoyloxy group, an aroyloxy group, a heterocyclylcarbonyloxy group, a carbamoyl group, a carboxy group, an alkylthio group, an arylthio group, an amino group, a cyano group, a dialkylphosphonate group, a diarylphosphonate group, a dialkylphosphinate group, a diarylphosphinate group, an organic group having a part of hydrogen atoms of these organic groups being substituted, a hydrogen atom, or a halogen atom.

M represents potassium, lithium, sodium, calcium, beryllium, zinc, copper, iron, magnesium, aluminum, cobalt, nickel, ammonium, a primary ammonium cation, a secondary ammonium cation, a tertiary ammonium cation, a quaternary ammonium cation, a phosphonium cation, or a phosphazene cation.

n represents an integer of 1 to 3.]

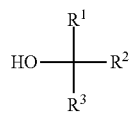
(5)

[In the formula (5), $R^1$ and $R^2$ each independently represent an alkyl group having 1 or more carbon atoms, an alkenyl group having two or more carbon atoms, an alkynyl group having two or more carbon atoms, an aryl group having 6 or more carbon atoms with an optional substituent group, an aralkyl group having 6 or more carbon atoms with an optional substituent group, a hydrogen atom, or a halogen atom; and $R^3$ represents an aryl group having 6 or more carbon atoms with an optional substituent group, or an aralkyl group having 6 or more carbon atoms with an optional substituent group.]

Examples of the organic group represented by Z in the formula (4) include those exemplified as the organic group represented by Z in the formula (1). Further, in the formula (4), Z is preferably an alkyl group having 1 to 18 carbon atoms, an alkoxy group having 1 to 18 carbon atoms, an aryloxy group having 6 to 20 carbon atoms, or a structure represented by the formulae (11) to (16), more preferably a structure represented by the formula (12), and even more preferably 3,5-dimethyl-1H-pyrazol-1-yl group.

Examples of M in the formula (4) include potassium, lithium, sodium, calcium, beryllium, zinc, copper, iron, magnesium, aluminum, cobalt, nickel, ammonium, a primary ammonium cation, a secondary ammonium cation, a tertiary ammonium cation, a quaternary ammonium cation, a phosphonium cation, and a phosphazene cation.

The dithiocarboxylic acid metal salt represented by the formula (4) is preferably a dithiocarboxylic acid metal salt represented by a formula (6).

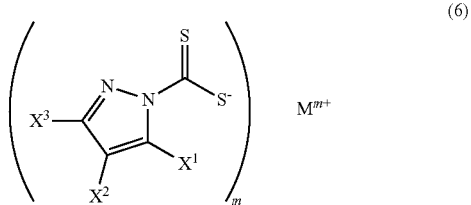

(6)

[In the formula (6), $X^1$ to $X^3$ each independently represent an alkyl group having 1 or more carbon atoms, an aryl group having 6 or more carbon atoms, an aralkyl group having 6 or more carbon atoms, a hydrogen atom, or a halogen atom.

M represents potassium, lithium, sodium, calcium, beryllium, zinc, copper, iron, magnesium, aluminum, cobalt, nickel, ammonium, a primary ammonium cation, a secondary ammonium cation, a tertiary ammonium cation, a quaternary ammonium cation, a phosphonium cation, or a phosphazene cation.

m represents an integer of 1 to 3.]

Examples of the alkyl group having 1 or more carbon atoms, aryl group having 6 or more carbon atoms and aralkyl group having 6 or more carbon atoms represented by $X^1$ to $X^3$ in the formula (6) include those exemplified as $X^1$ to $X^3$ in the formula (3). $X^1$ to $X^3$ in the formula (6) are preferably an alkyl group having 1 or more carbon atoms or a hydrogen atom.

Examples of the alkyl group having 1 or more carbon atoms, alkenyl group having two or more carbon atoms, alkynyl group having two or more carbon atoms, aryl group having 6 or more carbon atoms with an optional substituent group and aralkyl group having 6 or more carbon atoms with an optional substituent group represented by $R^1$ and $R^2$ include those exemplified as $R^1$ and $R^2$ in the formula (1). In the formula (5), $R^1$ and $R^2$ are preferably an alkyl group having 1 or more carbon atoms, more preferably an alkyl group having 1 to 5 carbon atoms, and most preferably a methyl group, an ethyl group, a propyl group, an isopropyl group, a n-butyl group, a s-butyl group, a t-butyl group, a n-pentyl group, a s-pentyl group, a t-pentyl group, a 3-pentyl group, an isopentyl group, or a neopentyl group.

Examples of the aryl group having 6 or more carbon atoms with an optional substituent group and aralkyl group having 6 or more carbon atoms with an optional substituent group represented by $R^3$ in the formula (5) include those exemplified as $R^3$ in the formula (1). In the formula (5), $R^3$ is preferably a structure represented by the formula (2), more preferably a phenyl group.

Preferable examples of the alcohol represented by the formula (5) include α-cumyl alcohol, benzyl alcohol, α-methylbenzyl alcohol, α-diethylbenzyl alcohol, α-ethylbenzyl alcohol, α-methylethylbenzyl alcohol, 4-methylbenzyl alcohol, 3-methylbenzyl alcohol, 2-methylbenzyl alcohol, 4-t-butylbenzyl alcohol, 1-naphthalene methanol, and 2-naphthalene methanol.

The method of carrying out the reaction between the dithiocarboxylic acid metal salt and the alcohol is not particularly limited, and examples thereof include a method of mixing the dithiocarboxylic acid metal salt and the alcohol in the presence of [bis(trifluoroacetoxy)iodo]benzene.

The amount of [bis(trifluoroacetoxy)iodo]benzene is preferably 0.01 mole or more, more preferably 0.05 mole or more, and even more preferably 0.1 mole or more, and is preferably 20 moles or less, more preferably 10 moles or less, and even more preferably 5 moles or less, with respect to 1 mole of the dithiocarboxylic acid metal salt.

The amount of the alcohol is preferably 1 mole or more, more preferably 5 moles or more, and even more preferably 10 moles or more, and is preferably 500 moles or less, more preferably 200 moles or less, and even more preferably 100 moles or less, with respect to 1 mole of the dithiocarboxylic acid metal salt.

A solvent may be added when mixing the dithiocarboxylic acid metal salt and the alcohol. Examples of the solvent include a halogen solvent such as dichloroethane and chloroform; an ether solvent such as tetrahydrofuran (THF) and diethylether; a ketone solvent such as acetone and methylethyl ketone; an aromatic solvent such as toluene and xylene; an ester solvent such as ethyl acetate; an aliphatic solvent such as hexane and cyclohexane; dimethyl formamide (DMF); dimethyl sulfoxide (DMSO); and pyridine. The amount of the solvent can be appropriately adjusted in accordance with the viscosity of the reaction liquid.

The temperature of the reaction liquid when mixing the dithiocarboxylic acid metal salt and the alcohol is preferably −78° C. or more, more preferably −50° C. or more, and even more preferably −30° C. or more, and is preferably 150° C. or less, more preferably 120° C. or less, and even more preferably 100° C. or less.

The time of mixing the dithiocarboxylic acid metal salt and the alcohol (reaction time) is preferably 1 hour or more, more preferably 2 hours or more, and even more preferably 5 hours or more, and is preferably 120 hours or less, more preferably 96 hours or less, and even more preferably 72 hours or less.

After the reaction between the dithiocarboxylic acid metal salt and the alcohol is over, the unreacted alcohol and the solvent if added are removed to obtain the reaction product.

Examples of the method for removing the unreacted alcohol and the solvent include a method of distilling under reduced pressure.

Since the reaction product contains by-products in addition to the target dithioester compound, the reaction product is preferably purified. The purification method is not particularly limited, and examples thereof include silica gel column chromatography.

It is considered that, in the production method of the dithioester compound, if the alcohol represented by the formula (5) is changed to a compound represented by the following formula (25) or formula (26), the dithioester compound represented by the formula (21) or the formula (22) can also be produced.

(25)

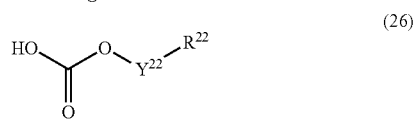

(26)

[In the formulae (25) and (26), $R^{21}$ and $R^{22}$ represent an aryl group with an optional substituent group; $Y^{21}$ and $Y^{22}$ represent an alkylene group having 10 or less carbon atoms, an alkenylene group having 10 or less carbon atoms, —$R^{23}$—C(=O)—$R^{24}$—, or a single bond; and $R^{23}$ and $R^{24}$ represent an alkylene group having 10 or less carbon atoms, or an alkenylene group having 10 or less carbon atoms. The substituent group optionally included in the aryl group is an alkyl group having 1 to 12 carbon atoms, an alkenyl group having 2 to 13 carbon atoms, an alkynyl group having 2 to 13 carbon atoms, a carboxy group, or a halogen atom.

It is noted that the alkyl group, alkenyl group, alkynyl group, alkylene group and alkenylene group include a linear group, a branched group, and a cyclic group.]

Examples

Next, the present invention will be described in detail by way of examples. However, the present invention is not limited to the examples described below. Various changes and modifications without departing from the spirit of the present invention are included in the scope of the present invention.

[Evaluation Method]

(1) $^1$H NMR $^1$H-NMR was measured with a nuclear magnetic resonance (NMR) tester (Model: AVANCE 500 (frequency: 500 MHz) available from Burker Corporation). CDCl$_3$ was used as the solvent.

(2) Electron Ionization Mass Spectrograph (EI-MS)

The mass analysis was performed with a mass analyzer (Model: JMS-700AM available from JEOL Corporation).

Synthesis of potassium
3,5-dimethyl-1H-pyrazol-1-dithiocarboxylate

In a one-necked flask having a volume of 100 mL and provided with a stirrer, 1.86 g (20.0 mmol) of 3,5-dimethylpyrazol was added, 30.0 mL of tetrahydrofuran was added, and further 1.16 g (20.6 mmol) of potassium hydroxide powder was added, and the mixture was stirred to obtain a light yellow solution.

Subsequently, 1.98 g (26.0 mmol) of carbon disulfide was added dropwise in the solution while being stirred. One hour later after the dropwise addition was over, the deposited precipitate was filtered out with a Kiriyama type funnel. The filtered product was washed with diethyl ether and then dried at 50° C. under reduced pressure to obtain potassium 3,5-dimethyl-1H-pyrazol-1-dithiocarboxylate represented by a formula (7).

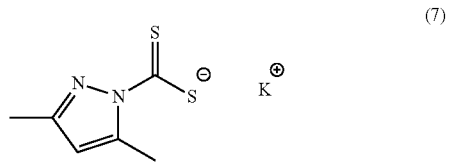

(7)

Synthesis of dithioester compound No. 1

In a one-necked flask (100 mL) provided with a stirrer, 860 mg (2.00 mmol) of [bis(trifluoroacetoxy)iodo]benzene was added under a nitrogen gas atmosphere. Subsequently, 4.0 mL of α-cumyl alcohol was added in the flask and stirred to obtain a light yellow solution. Next, 438 mg (2.00 mmol) of potassium 3,5-dimethyl-1H-pyrazol-1-dithiocarboxylate was added in the light yellow solution and stirred at room temperature for 16.5 hours. After the predetermined period of time, the reaction solution was concentrated under reduced pressure. The obtained concentrated liquid was purified by silica gel column chromatography to obtain 24.5 mg of a dithioester compound No. 1.

Figure 2:
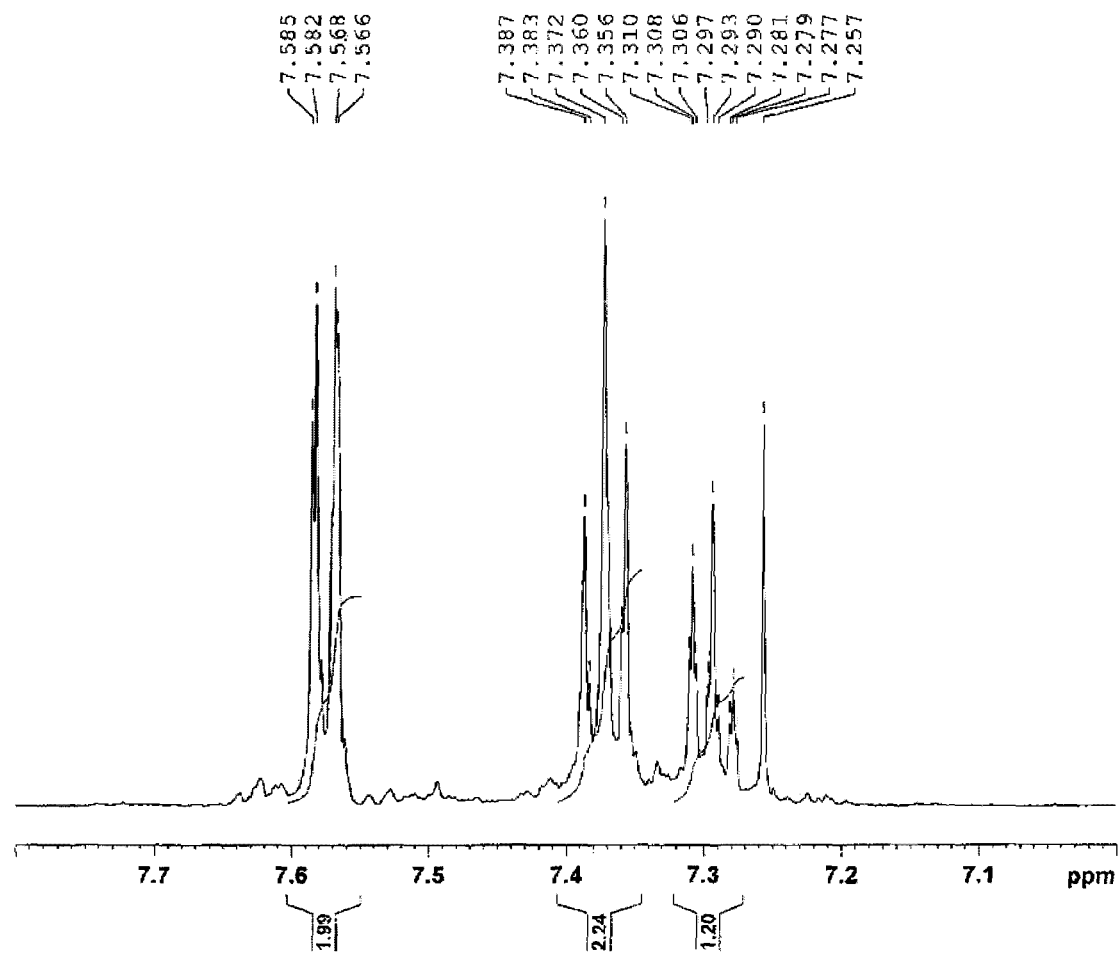
FIG. 2 is $^1$H-NMR spectrum of dithioester compound No. 1.
Figure 3:
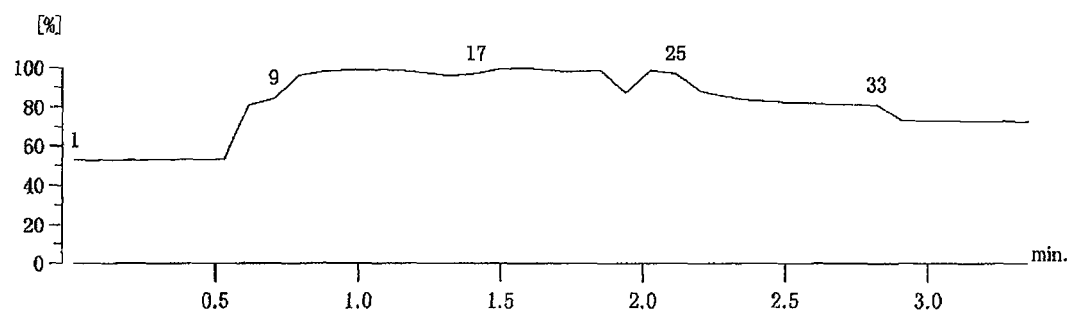
FIG. 3 is MS spectrum of dithioester compound No. 1.
Figure 3:
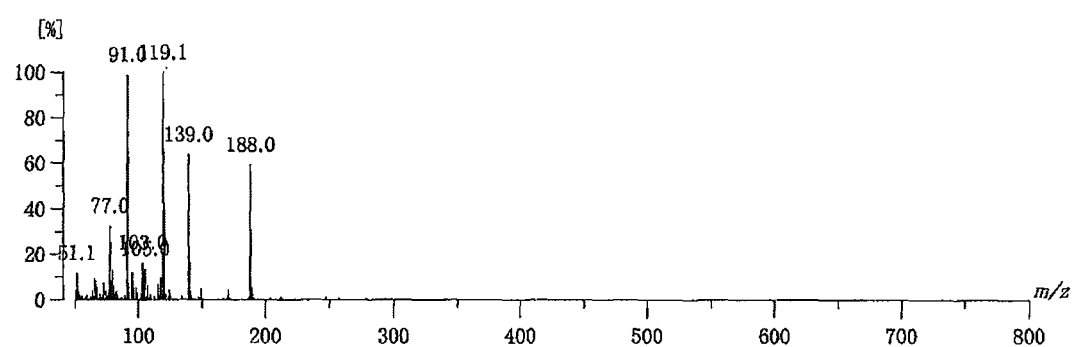
Figure 3:
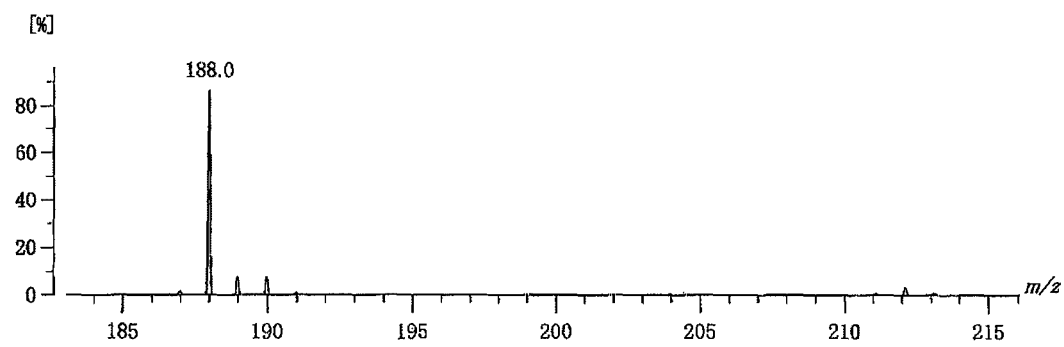

$^1$H NMR measurement and EI-MS measurement were performed for the dithioester compound No. 1 obtained above. The results are shown in FIGS. 1 to 3. Based on the results of $^1$H NMR measurement and EI-MS measurement shown in FIGS. 1 to 3, it is confirmed that the obtained dithioester compound No. 1 is a compound represented by a formula (8).

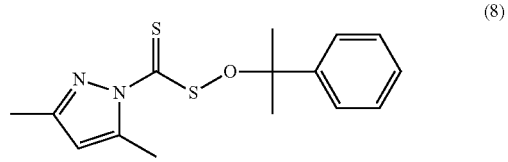 [SMILES: Cc1cc(C)n(C(=S)SOC(C)(C)c2ccccc2)n1]

(8)

Synthesis of Dithioester Compound No. 2

In a one-necked flask (100 mL) provided with a stirrer, 860 mg (2.00 mmol) of [bis(trifluoroacetoxy)iodo]benzene was added under a nitrogen gas atmosphere. Subsequently, 4.0 mL of α-cumyl alcohol was added in the flask and stirred to obtain a light yellow solution. Next, 1.31 g (6.00 mmol) of potassium 3,5-dimethyl-1H-pyrazol-1-dithiocarboxylate was added in the light yellow solution and stirred at room temperature for 21.5 hours. After the predetermined period of time, the reaction solution was concentrated under reduced pressure. The obtained concentrated liquid was purified by silica gel column chromatography to obtain 95.3 mg of a dithioester compound No. 2.

Figure 4:
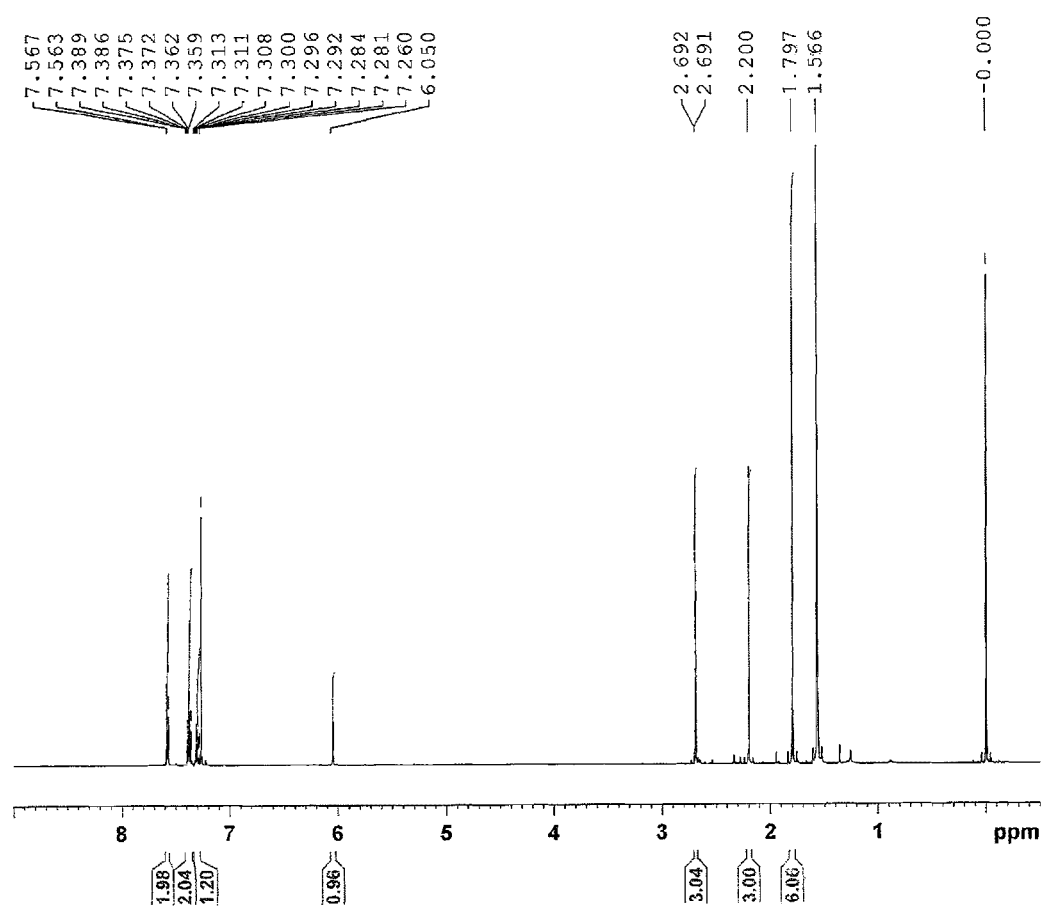
FIG. 4 is $^1$H-NMR spectrum of dithioester compound No. 2.

$^1$H NMR measurement was performed for the dithioester compound No. 2 obtained above. The result is shown in FIG. 4. Based on the result of $^1$H NMR measurement shown in FIG. 4, it is confirmed that the obtained dithioester compound No. 2 is a compound represented by the formula (8).

Synthesis of Dithioester Compound No. 3

In a three-necked flask (1 L) provided with a stirrer, 67.30 g (156.5 mmol) of [bis(trifluoroacetoxy)iodo]benzene was added under a nitrogen gas atmosphere. Subsequently, 313.0 mL of α-cumyl alcohol was added in the flask and stirred to obtain a light yellow solution. Next, 102.9 g (469.5 mmol) of potassium 3,5-dimethyl-1H-pyrazol-1-dithiocarboxylate was added in the light yellow solution and stirred at room temperature for 18 hours. After the predetermined period of time, the reaction solution was filtered to remove insoluble substances, and concentrated under reduced pressure. The obtained concentrated liquid was purified by silica gel column chromatography to obtain 2.62 g of a dithioester compound No. 3.

$^1$H NMR measurement was performed for the dithioester compound No. 3 obtained above. Based on the result of $^1$H NMR measurement, it is confirmed that the obtained dithioester compound No. 3 is a compound represented by the formula (8).

The dithioester compound according to the present invention generates an aralkyloxy radical ($R^1R^2R^3CO\cdot$). This aralkyloxy radical has high ability of abstracting hydrogen. Thus, the dithioester compound according to the present invention is suitably used as an additive (RAFT agent) when synthesizing a polymer material having a crosslinked structure.

This application is based on Japanese patent application No. 2019-228268 filed on Dec. 18, 2019, the contents of which are hereby incorporated by reference.

The invention claimed is:

1. A dithioester compound represented by a formula (1):

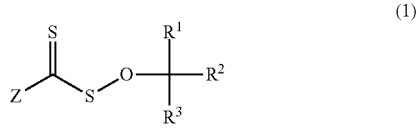

(1)

wherein in the formula (1), $R^1$ and $R^2$ each independently represent an alkyl group having 1 or more carbon atoms, an alkenyl group having two or more carbon atoms, an alkynyl group having two or more carbon atoms, an aryl group having 6 or more carbon atoms with an optional substituent group, an aralkyl group having 6 or more carbon atoms with an optional substituent group, a hydrogen atom, or a halogen atom;

$R^3$ represents an aryl group having 6 or more carbon atoms with an optional substituent group, or an aralkyl group having 6 or more carbon atoms with an optional substituent group; and Z represents an alkyl group, an alkenyl group, an alkynyl group, an aryl group, an aralkyl group, a heterocyclyl group, an alkoxy group, an aryloxy group, an aralkyloxy group, a heterocyclyloxy group, an alkanoyl group, an aroyl group, a heterocyclylcarbonyl group, an alkoxycarbonyl group, an aryloxycarbonyl group, a heterocyclyloxycarbonyl group, an alkanoyloxy group, an aroyloxy group, a heterocyclylcarbonyloxy group, a carbamoyl group, a carboxy group, an alkylthio group, an arylthio group, an amino group, a cyano group, a dialkylphosphonate group, a diarylphosphonate group, a dialkylphosphinate group, a diarylphosphinate group, a cyanoalkyl group, a halogenated alkyl group, a hydrogen atom, or a halogen atom.

2. The dithioester compound according to claim 1, wherein in the formula (1), $R^3$ is a structure represented by a formula (2):

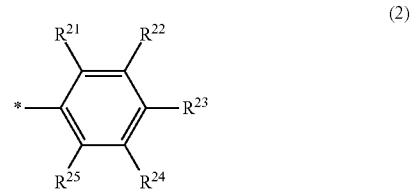

(2)

wherein in the formula (2), $R^{21}$ to $R^{25}$ each independently represent an alkyl group having 1 or more carbon atoms, an alkenyl group having two or more carbon atoms, an alkynyl group having two or more carbon atoms, an aryl group having 6 or more carbon atoms, an aralkyl group having 6 or more carbon atoms, a hydrogen atom, or a halogen atom.

3. A method for producing the dithioester according to claim 1, comprising carrying out a reaction between a dithiocarboxylic acid metal salt represented by a formula (4) and an alcohol represented by a formula (5) in the presence of [bis(trifluoroacetoxy)iodo]benzene,

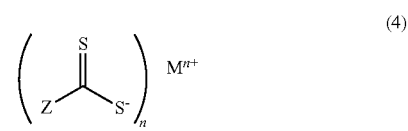

(4)

wherein in the formula (4),

Z represents an alkyl group, an alkenyl group, an alkynyl group, an aryl group, an aralkyl group, a heterocyclyl group, an alkoxy group, an aryloxy group, an aralkyloxy group, a heterocyclyloxy group, an alkanoyl group, an aroyl group, a heterocyclylcarbonyl group, an alkoxycarbonyl group, an aryloxycarbonyl group, a heterocyclyloxycarbonyl group, an alkanoyloxy group, an aroyloxy group, a heterocyclylcarbonyloxy group, a carbamoyl group, a carboxy group, an alkylthio group, an arylthio group, an amino group, a cyano group, a dialkylphosphonate group, a diarylphosphonate group, a dialkylphosphinate group, a diarylphosphinate group, a cyanoalkyl group, a halogenated alkyl group, a hydrogen atom, or a halogen atom;

M represents potassium, lithium, sodium, calcium, beryllium, zinc, copper, iron, magnesium, aluminum, cobalt, nickel, ammonium, a primary ammonium cation, a secondary ammonium cation, a tertiary ammonium cation, a quaternary ammonium cation, a phosphonium cation, or a phosphazene cation; and n represents an integer of 1 to 3,

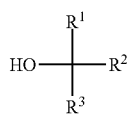
(5)

wherein in the formula (5),

R¹ and R² each independently represent an alkyl group having 1 or more carbon atoms, an alkenyl group having two or more carbon atoms, an alkynyl group having two or more carbon atoms, an aryl group having 6 or more carbon atoms with an optional substituent group, an aralkyl group having 6 or more carbon atoms with an optional substituent group, a hydrogen atom, or a halogen atom; and R³ represents an aryl group having 6 or more carbon atoms with an optional substituent group, or an aralkyl group having 6 or more carbon atoms with an optional substituent group.

4. The method according to claim 3, wherein an amount of [bis(trifluoroacetoxy)iodo]benzene ranges from 0.01 mole to 20 moles with respect to 1 mole of the dithiocarboxylic acid metal salt.

5. The method according to claim 3, wherein an amount of the alcohol ranges from 1 mole to 500 moles with respect to 1 mole of the dithiocarboxylic acid metal salt.

6. A dithioester compound represented by a formula (1):

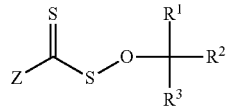
(1)

wherein in the formula (1),

R¹ and R² each independently represent an alkyl group having 1 or more carbon atoms, an alkenyl group having two or more carbon atoms, an alkynyl group having two or more carbon atoms, an aryl group having 6 or more carbon atoms with an optional substituent group, an aralkyl group having 6 or more carbon atoms with an optional substituent group, a hydrogen atom, or a halogen atom;

R³ represents an aryl group having 6 or more carbon atoms with an optional substituent group, or an aralkyl group having 6 or more carbon atoms with an optional substituent group; and Z represents an alkyl group having 1 to 18 carbon atoms, an alkoxy group having 1 to 18 carbon atoms, an aryloxy group having 6 to 20 carbon atoms, an oxopyrrolidine-1-yl group, a methylphenylamino group, a methylpyridylamino group, a cyanomethyl group, a 2-cyanobutane-2-yl group, a 1-cyanoethane-1-yl group, a 2-cyanopropane-2-yl group, a 2-phenylpropane-2-yl group, a 1-cyano-1-phenylethane-1-yl group, a 2-(ethoxycarbonyl)propane-2-yl group, or a structure represented by formulae (11) to (13), (15) and (16):

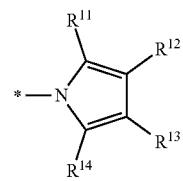
(11)

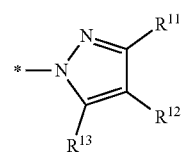
(12)

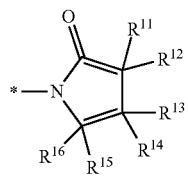
(13)

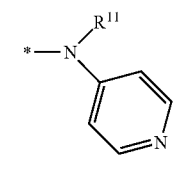
(15)

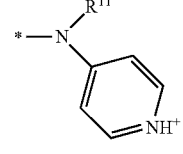
(16)

wherein in the formulae (11) to (13), (15) and (16),

R¹¹ to R¹⁶ represent an alkyl group having 1 to 18 carbon atoms, an aryl group having 6 to 20 carbon atoms, an aralkyl group having 6 to 20 carbon atoms, a hydrogen atom, or a halogen atom.

7. The dithioester compound according to claim 6, wherein in the formula (1), R³ is a structure represented by a formula (2):

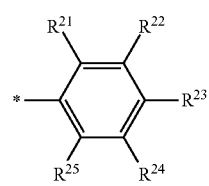
(2)

wherein in the formula (2), R²¹ to R²⁵ each independently represent an alkyl group having 1 or more carbon atoms, an alkenyl group having two or more carbon atoms, an alkynyl group having two or more carbon atoms, an aryl group having 6 or more carbon atoms, an aralkyl group having 6 or more carbon atoms, a hydrogen atom, or a halogen atom.

8. The dithioester compound according to claim 6, wherein the compound represented by the formula (1) is a compound represented by a formula (3):

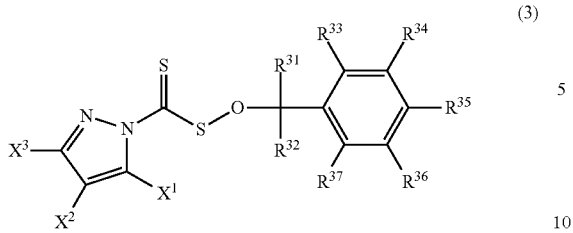
(3)

wherein in the formula (3), $R^{31}$ to $R^{37}$ each independently represent an alkyl group having 1 or more carbon atoms, an alkenyl group having two or more carbon atoms, an alkynyl group having two or more carbon atoms, an aryl group having 6 or more carbon atoms, an aralkyl group having 6 or more carbon atoms, a hydrogen atom, or a halogen atom; and $X^1$ to $X^3$ each independently represent an alkyl group having 1 or more carbon atoms, an aryl group having 6 or more carbon atoms, an aralkyl group having 6 or more carbon atoms, a hydrogen atom, or a halogen atom.

9. The dithioester compound according to claim 8, wherein $R^{31}$ to $R^{37}$ each independently represent an alkyl group having 1 or more carbon atoms or a hydrogen atom in the formula (3).

10. The dithioester compound according to claim 8, wherein $X^1$ to $X^3$ each independently represent an alkyl group having 1 or more carbon atoms or a hydrogen atom in the formula (3).

11. The dithioester compound according to claim 9, wherein $X^1$ to $X^3$ each independently represent an alkyl group having 1 or more carbon atoms or a hydrogen atom in the formula (3).

12. The dithioester compound according to claim 9, wherein $R^{31}$ and $R^{32}$ each independently represent an alkyl group having 1 to 5 carbon atoms in the formula (3).

13. The dithioester compound according to claim 9, wherein $R^{33}$ to $R^{37}$ each independently represent an alkyl group having 1 or more carbon atoms or a hydrogen in the formula (3).

14. The dithioester compound according to claim 9, wherein $R^{31}$ and $R^{32}$ each independently represent an alkyl group having 1 to 5 carbon atoms, and $R^{33}$ to $R^{37}$ each independently represent an alkyl group having 1 or more carbon atoms or a hydrogen in the formula (3).

15. The dithioester compound according to claim 14, wherein $X^1$ to $X^3$ each independently represent an alkyl group having 1 or more carbon atoms or a hydrogen atom in the formula (3).

16. The dithioester compound according to claim 9, wherein $R^{31}$ and $R^{32}$ are a methyl group, $R^{33}$ to $R^{37}$ are a hydrogen atom, $X^1$ and $X^3$ are a methyl group, and $X^2$ is a hydrogen atom in the formula (3).

17. A method for producing the dithioester according to claim 6, comprising carrying out a reaction between a dithiocarboxylic acid metal salt represented by a formula (4) and an alcohol represented by a formula (5) in the presence of [bis(trifluoroacetoxy)iodo]benzene,

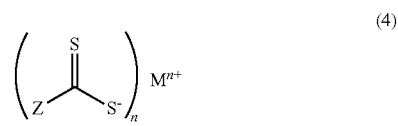
(4)

wherein in the formula (4),

Z represents an alkyl group having 1 to 18 carbon atoms, an alkoxy group having 1 to 18 carbon atoms, an aryloxy group having 6 to 20 carbon atoms, an oxopyrrolidine-1-yl group, a methylphenylamino group, a methylpyridylamino group, a cyanomethyl group, a 2-cyanobutane-2-yl group, a 1-cyanoethane-1-yl group, a 2-cyanopropane-2-yl group, a 2-phenylpropane-2-yl group, a 1-cyano-1-phenylethane-1-yl group, a 2-(ethoxycarbonyl)propane-2-yl group, or a structure represented by formulae (11) to (13), (15) and (16):

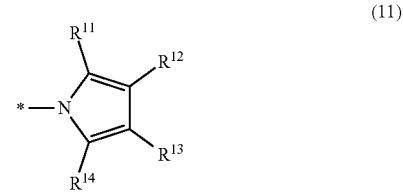
(11)

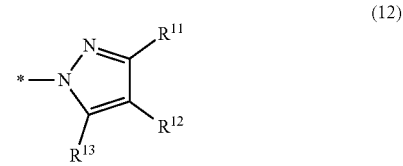
(12)

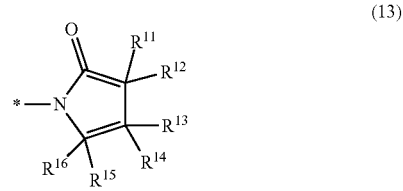
(13)

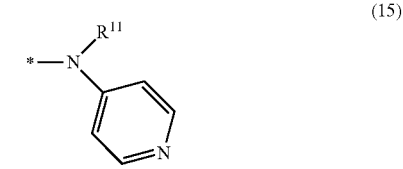
(15)

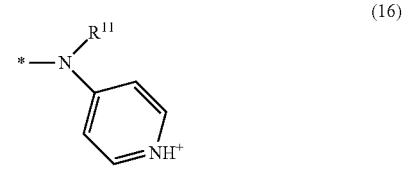
(16)

wherein in the formulae (11) to (13), (15) and (16), $R^{11}$ to $R^{16}$ represent an alkyl group having 1 to 18 carbon atoms, an aryl group having 6 to 20 carbon atoms, an aralkyl group having 6 to 20 carbon atoms, a hydrogen atom, or a halogen atom;

M represents potassium, lithium, sodium, calcium, beryllium, zinc, copper, iron, magnesium, aluminum, cobalt, nickel, ammonium, a primary ammonium cation, a secondary ammonium cation, a tertiary ammonium cation, a quaternary ammonium cation, a phosphonium cation, or a phosphazene cation; and n represents an integer of 1 to 3,

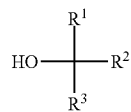 (5)

wherein in the formula (5), $R^1$ and $R^2$ each independently represent an alkyl group having 1 or more carbon atoms, an alkenyl group having two or more carbon atoms, an alkynyl group having two or more carbon atoms, an aryl group having 6 or more carbon atoms with an optional substituent group, an aralkyl group having 6 or more carbon atoms with an optional substituent group, a hydrogen atom, or a halogen atom; and $R^3$ represents an aryl group having 6 or more carbon atoms with an optional substituent group, or an aralkyl group having 6 or more carbon atoms with an optional substituent group.

18. The method according to claim 17, wherein the dithiocarboxylic acid metal salt represented by the formula (4) is a dithiocarboxylic acid metal salt represented by a formula (6):

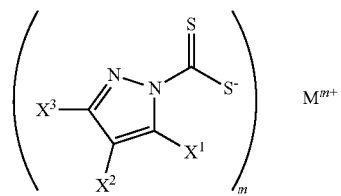 (6)

wherein in the formula (6), $X^1$ to $X^3$ each independently represent an alkyl group having 1 or more carbon atoms, an aryl group having 6 or more carbon atoms, an aralkyl group having 6 or more carbon atoms, a hydrogen atom, or a halogen atom;

M represents potassium, lithium, sodium, calcium, beryllium, zinc, copper, iron, magnesium, aluminum, cobalt, nickel, ammonium, a primary ammonium cation, a secondary ammonium cation, a tertiary ammonium cation, a quaternary ammonium cation, a phosphonium cation, or a phosphazene cation; and m represents an integer of 1 to 3.

19. The method according to claim 17, wherein an amount of [bis(trifluoroacetoxy)iodo]benzene ranges from 0.01 mole to 20 moles with respect to 1 mole of the dithiocarboxylic acid metal salt.

20. The method according to claim 17, wherein an amount of the alcohol ranges from 1 mole to 500 moles with respect to 1 mole of the dithiocarboxylic acid metal salt.

* * * * *